United States Patent
Riordan et al.

(10) Patent No.: US 10,702,184 B2
(45) Date of Patent: Jul. 7, 2020

(54) LOW POWER MEASUREMENT OF SKIN ELECTRICAL PROPERTIES

(71) Applicant: Analog Devices International Unlimited Company, Limerick (IE)

(72) Inventors: Liam Riordan, Raheen (IE); José Carlos Conchell Añó, Valencia (ES); Tony Shi, Beijing (CN); Guangyang Qu, Beijing (CN); Hanqing Wang, Beijing (CN)

(73) Assignee: Analog Devices International Unlimited Company, Limerick Co. Limerick (IE)

( * ) Notice: Subject to any disclaimer, the term of this patent is extended or adjusted under 35 U.S.C. 154(b) by 479 days.

(21) Appl. No.: 15/616,807

(22) Filed: Jun. 7, 2017

(65) Prior Publication Data
US 2018/0353100 A1    Dec. 13, 2018

(51) Int. Cl.
*A61B 5/053*    (2006.01)
*A61B 5/00*    (2006.01)
*A61B 5/01*    (2006.01)

(52) U.S. Cl.
CPC .......... *A61B 5/0531* (2013.01); *A61B 5/0533* (2013.01); *A61B 5/7225* (2013.01);
(Continued)

(58) Field of Classification Search
CPC ... A61B 5/0531; A61B 5/0533; A61B 5/7257; A61B 5/7225; A61B 2560/0247;
(Continued)

(56) References Cited

U.S. PATENT DOCUMENTS

| 5,178,154 A | 1/1993 | Ackmann et al. |
| 5,428,638 A | 6/1995 | Cioffi |

(Continued)

FOREIGN PATENT DOCUMENTS

| EP | 2759261 A1 | 7/2014 |
| WO | WO-2006029035 A1 | 3/2006 |
| WO | WO-2014147024 A1 | 9/2014 |

OTHER PUBLICATIONS

"Analog Devices 1 MSPS, 12-Bit Impendance Converter, Network Analyzer", Data Sheet, AD 6933, Rev. E, (c) 2005-2013, Analog Devices, Inc., (2005-2013), 43 pgs.
(Continued)

*Primary Examiner* — Eric F Winakur
*Assistant Examiner* — Abid A Mustansir
(74) *Attorney, Agent, or Firm* — Schwegman Lundberg & Woessner, P.A.

(57) ABSTRACT

Various examples are directed to a measurement system for measuring an electrical property of skin comprising an excitation circuit, a receiver circuit, and a sequencer circuit. The excitation circuit may generate a periodic excitation signal that, when provided to the skin, generates a response signal in the skin indicative of the electrical property. The sequencer circuit may be configured to activate the excitation circuit to provide the excitation signal to the skin. While the excitation circuit is activated to provide the excitation signal to the skin, the sequencer circuit may activate the receiver circuit to execute a first sample cycle to generate a first plurality of samples of the response signal. A first value for the electrical property of the skin may be determined based at least in part on the first plurality of samples of the response signal.

21 Claims, 9 Drawing Sheets

(52) U.S. Cl.
CPC .............. *A61B 5/7257* (2013.01); *A61B 5/01* (2013.01); *A61B 2560/0247* (2013.01)

(58) Field of Classification Search
CPC .... A61B 5/01; A61B 5/72; A61B 5/05; A61B 5/441; A61B 5/053; G01N 27/00
See application file for complete search history.

(56) References Cited

U.S. PATENT DOCUMENTS

| | | | |
|---|---|---|---|
| 5,916,237 | A | 6/1999 | Schu et al. |
| 5,919,142 | A | 7/1999 | Boone et al. |
| 6,167,303 | A | 12/2000 | Thompson |
| 8,140,143 | B2 | 3/2012 | Picard et al. |
| 2006/0052678 | A1 | 3/2006 | Drinan et al. |
| 2009/0264792 | A1* | 10/2009 | Mazar .................. A61B 5/0531 600/547 |
| 2011/0004072 | A1 | 1/2011 | Fletcher et al. |
| 2011/0092834 | A1 | 4/2011 | Yazicioglu et al. |
| 2013/0093501 | A1* | 4/2013 | Kajimoto ........... A61N 1/36014 327/517 |
| 2013/0271155 | A1 | 10/2013 | O'Keeffe et al. |

OTHER PUBLICATIONS

"Analogy Devices 16-Bit Precision, Low Power Metter on a Chip with Cortex-M3 and Connectivity", (c)2014 Analogy Devices, Inc., Data Sheet ADuCM350 Rev. A, (2014), 41 pgs.
"Semiconductor solutions for healthcare applications", (c) 2012 STMicroelectronics, (Apr. 2012), 12 pgs.
Brennan, Sean, "Measuring a Grounded Impedance Profile Using the AD5933", Analog Devices, AN-847 Application Note, (c) 2006-2012, (2006-2012), 12 pgs.
Chandrakasan, P Anantha, et al., "Ultralow-Power Electronics for Biomedical Applications", Annual Review BioMed. Eng., 10, (2008), 247-274.
Kamat, D. K., et al., "A Heart Rate Measurement using Bio-impedance Signal Analysis", International Journal of Advanced Research in Electrical, Electronics and Instrumentation Engineering, vol. 3, Issue 4, (Apr. 2014), 8446-8451.
Conchell, Jose C., "Design, Development and Evaluation of a System to Obtain Electroderrnal Activity", Analog Devices, Inc., (Sep. 22, 2016), 91 pgs.
"Netherlands Application Serial No. N2021077, Search Report dated Feb. 11, 2020", w/ English Translation, 13 pgs.
"UK Application Serial No. 1809195.9, Combined Search and Examination Report dated Dec. 24, 2018", 3 pgs.

* cited by examiner

LOW POWER MEASUREMENT OF SKIN ELECTRICAL PROPERTIES

FIELD OF THE DISCLOSURE

This document pertains generally, but not by way of limitation, to integrated circuits and, and particularly, but not by way of limitation, to integrated circuits for measuring electrical parameters of skin.

BACKGROUND

The electrical properties of an individual's skin can provide different types of information about the individual's health. For example, changes in the electrical properties of skin, referred to as Electrodermal Activity, can indicate an individual's level of stress as well as other health-related conditions.

SUMMARY OF THE DISCLOSURE

In various examples, a measurement system for measuring an electrical property of skin, such as skin impedance, has an excitation circuit including a digital waveform generator that generates a digital excitation signal at an excitation frequency. A digital-to-analog converter (DAC) converts the digital excitation signal to analog. The analog excitation signal is provided to skin to cause an AC current to flow through the skin from a first electrode to a second electrode. A receiver circuit is in electrical communication with the second electrode to receive a response signal. For example, the response signal may be or be proportional to the current caused in the skin in response to the excitation signal. The receiver circuit may include an analog-to-digital converter (ADC) that collects samples of the response signal. The samples may be used to generate a discrete Fourier transform (DFT) or other value that provides an indication of skin impedance. For example, the real component of the DFT corresponds to the ohmic resistance of the skin and the imaginary component of the DFT corresponds to the reactance of the skin.

BRIEF DESCRIPTION OF THE DRAWINGS

In the drawings, which are not necessarily drawn to scale, like numerals may describe similar components in different views. Eke numerals having different letter suffixes may represent different instances of similar components. The drawings illustrate generally, by way of example, but not by way of limitation, various embodiments discussed in the present document.

DETAILED DESCRIPTION

Figure 1:
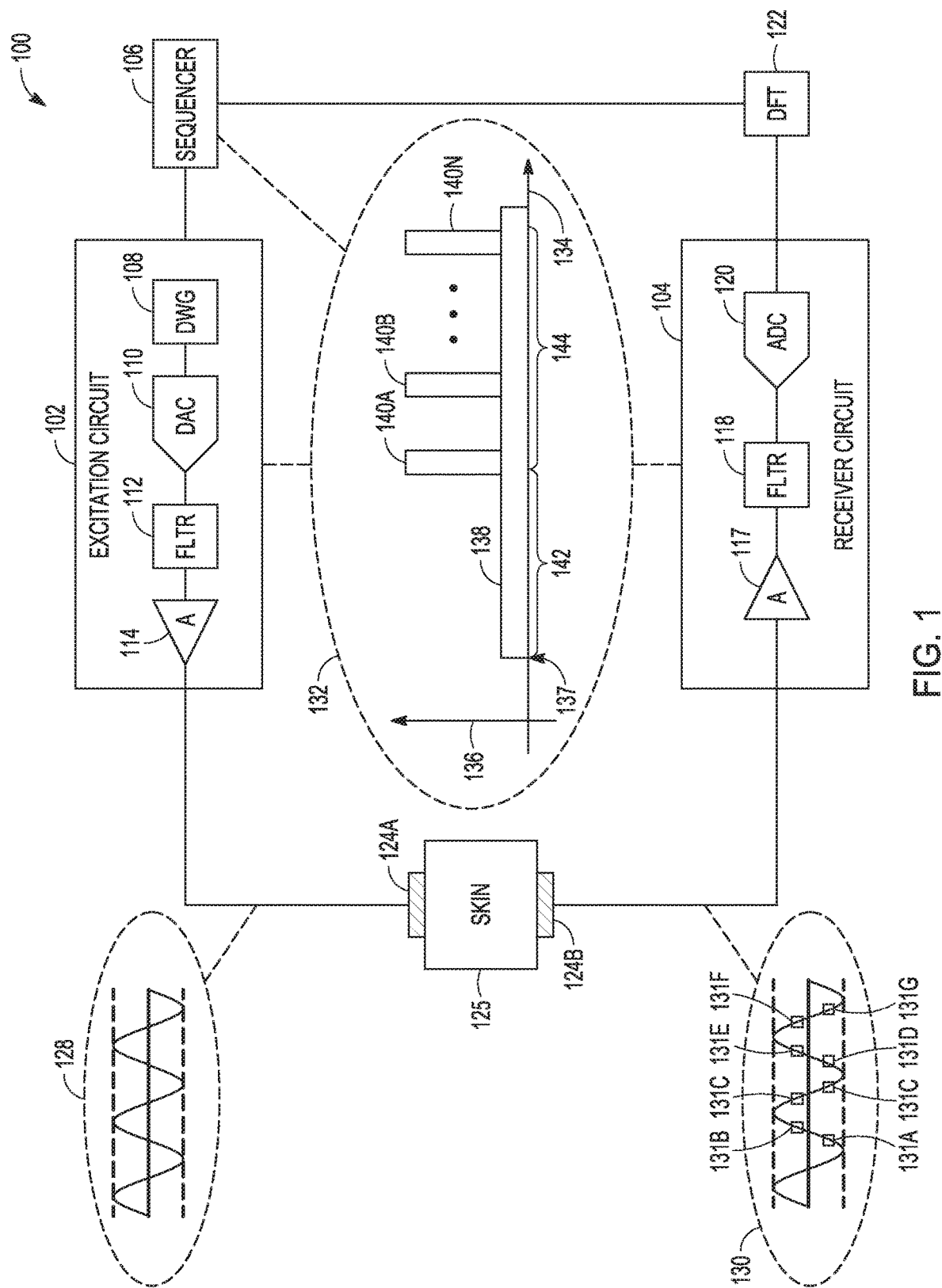
FIG. 1 is a block diagram showing one example of a measurement system for measuring skin impedance.

The electrical properties of skin may be measured as described herein, for example, to monitor patient health. Various electrical properties may be measured including, for example, skin impedance, a voltage drop across the skin, and/or a current through the skin. Measuring electrical properties such as these over time may provide an indication of EDA, which can indicate the patient's stress level as well as other health conditions. Some examples described herein measure skin impedance. Skin impedance may have two components, an ohmic resistance component at direct current (DC) and a reactance component at alternating current (AC). The total impedance of skin may be described with the ohmic resistance component indicated by a magnitude and the reactance indicated by a phase angle.

The measurement system described herein may be configured for low power operation, which may make it suitable for use in applications where low power consumption is desirable, such as battery powered devices. To save power, the measurement system may be configured to periodically activate and deactivate at least the receiver circuit. When the receiver circuit is activated, it may execute a sample cycle during which the receiver circuit captures a set of samples of the response signal. After the sample cycle, the receiver circuit is deactivated such that it does not consume power or consumes less power than during a sample cycle. In some examples, described herein, the receiver circuit, or parts thereof such as the ADC, are deactivated within a sample cycle between samples.

The receiver circuit may execute sample cycles periodically. For example, a sample cycle may be executed for a sample cycle time. The sample cycle time may correspond to a first number of response signal periods. After a sample cycle is executed, all or part of the receiver circuit is deactivated for a deactivation time. The deactivation time may correspond to a second number of response signal periods. In some examples, after the deactivation time has elapsed, the receiver circuit is re-activated to execute a next sample cycle, which may also be executed for the sample cycle time. To illustrate this concept, consider an example where the excitation signal and response signal are at 100 Hz. The measurement system may be configured to execute a sample cycle with the receiver circuit that generates 16 samples over a sample cycle time of about 50 ms, which corresponds to about 4 response signal periods. In this example, the receiver circuit may be deactivated for a deactivation time of about 200 ms, or about 16 response signal periods.

In some examples, the excitation circuit is configured to maintain the excitation signal for an excitation setup period before the receiver circuit executes a sample cycle. This may improve the operation of the system, for example, by lessening the impact of transient effects on the response signal. The interface between the skin and the electrodes that provide the excitation signal can have a natural potential difference, which may be as high as a few volts. To allow for this voltage offset, it is sometimes desirable to include one or more filtering capacitors in the measurement system. Also, the skin itself includes structures with reactive electrical properties (e.g., capacitance or inductance). After the excitation signal is turned on, the reactive components of the skin and the measurement system gather energy in a way that may distort the response signal and prevent accurate measuring of skin impedance. Maintaining the excitation signal for the excitation setup period may allow the reactive components of the measurement system and the skin to charge before measurements begin. Also, in some examples, turning on the excitation signal generates transients. These transients may affect the response signal and may also generate noise in measurements of other physiological electrical properties, such as an electrocardiogram (ECG), etc. For example, it may be desirable in some circumstances to have a device that includes a measurement system for measuring skin impedance and a measurement system for measuring an ECG. In such a system, a measurement system for skin impedance that generates transients affecting the ECG measurement may add design complications.

In some examples, the excitation circuit of the skin impedance measurement system is activated to maintain the excitation signal through multiple sample cycles of the receiver circuit (e.g., the excitation circuit is not turned off between sample cycles). This may further accentuate the benefits of the excitation setup period described above. For example, maintaining the excitation signal over multiple sample cycles of the receiver circuit may permit additional time for the reactive components of the skin and the measurement system to charge, further reducing distortions to the response signal. Also, in some examples, storing energy at the reactive components of the skin and the measurement system may require more power than maintaining the excitation signal. Accordingly, maintaining the excitation signal through multiple sample cycles of the receiver circuit may reduce the total power consumption of the measurement system.

FIG. 1 is a block diagram showing one example of a measurement system 100 for measuring skin impedance. The measurement system 100 includes an excitation circuit 102 and a receiver circuit 104. The excitation circuit 102 generates an excitation signal 128, which is provided to the skin 126 via the electrode 124A. The excitation signal 128, in some examples, is at a low frequency (e.g., between about 50 Hz and about 200 Hz) so as to prevent the excitation signal from penetrating beyond the upper layers of the skin. The excitation signal 128 causes a response signal 130 in the skin. The response signal 130 may be indicative of the EDA. For example, a current of the response signal 130 may be used, as described herein, to find skin resistance. The skin resistance may be indicative of EDA.

The response signal 130 is received at the electrode 124B. For example, the response signal 130 may be or be proportional to the current generated in the skin 126 in response to the excitation signal 128. In some examples, the measurement system 100 may be incorporated into a device that is configured to place the electrodes 124A, 124B in contact with the user's skin, for example, at the wrist. The receiver circuit 104 receives and samples the response signal 130. A discrete Fourier transform (DFT) of the samples provides a measure of the impedance of the skin 126, as described above.

The excitation signal 128 may be any suitable signal at any suitable frequency. For example, the excitation signal 128 may have an excitation frequency between about 10 Hz and about 150 Hz. In some examples, the excitation signal 128 has a frequency of about 100 Hz or about 120 Hz. The response signal 130 may represent the current generated in the skin 126 in response to the excitation signal 128. The response signal 130 may be of about the same frequency as the excitation signal 128, but may be of a different magnitude than the excitation signal 128 (e.g., due to ohmic resistance in the skin 126) and offset in phase from the excitation signal 128 (e.g., due to reactance in the skin 126).

The excitation circuit 102 may include a digital waveform generator 108, a DAC 110, a filter 112, and an amplifier 114. The digital waveform generator 108 may generate a digital excitation waveform at the excitation frequency. The DAC 110 converts the digital excitation waveform to analog. In some examples, the DAC 110 is a 12-bit DAC and may be a low power DAC. For example, the DAC 110, filter 112, and amplifier 114 may be configured to draw low levels of current, minimizing power as the excitation circuit 102 is active. In some examples, the DAC 110 draws current of between about 0.5 uA and about 2 uA, in some examples, about 1 uA. The amplifier 114 may draw current of between about 1.1 uA and 4.6 uA, in some examples about 2.3 uA. In some examples, the DAC 110 includes or is in communication with an optional excitation buffer. The excitation buffer may draw current of between about 1.1 uA and 4.6 uA, in some examples about 2.3 uA.

The filter 112 filters the excitation signal 128, to remove artifacts from the conversion to analog. The filter 112 may be a low-pass filter that removes higher-frequency components from the excitation signal 128. In some examples, the filter 112 is or includes a raised cosine filter. In some examples, the filter 112 is omitted. For example, the digital waveform generator 108 and/or DAC 110 may be selected with a resolution (e.g., number of bits) high enough to obviate the need for the filter 112. In other examples, the digital waveform generator 108 and/or DAC 110 may have of a low resolution, which may create high frequency artifacts in the excitation signal 128 that may be removed by the filter 112. An amplifier 114 may amplify the excitation signal for provision to the skin 126 via the electrodes 124A, 124B.

As described above, the response signal 130 received at the electrode 124B may be or be indicative of a current in the skin 126 between the electrodes 124A, 124B that results from the excitation signal 128. The response signal 130 may be provided to the receiver circuit 104, which may include an amplifier 116, a filter 118, an ADC 120, and a DFT circuit 122. The amplifier 116 may amplify the response signal 130 for further processing. In some examples, the amplifier 116 is or includes a transimpedance amplifier or other suitable circuit that converts a received current to a voltage. A filter 118 may be or include an anti-aliasing filter. For example, the filter 118 may be a bandpass filter that limits the bandwidth of the response signal 130 to a band of interest so as to avoid aliasing at the ADC 120.

In some examples, the ADC 120 is configured to sample the response signal 130 at a sampling frequency. Example samples 131A-G are shown in FIG. 1. In some examples, the ADC 120 is configured to oversample the response signal 130. Oversampling the response signal 130 may include sampling at a frequency higher than the Nyquist frequency for the response signal 130. The Nyquist frequency is the lowest frequency at which a signal can be sampled without introducing aliasing errors. For example, the Nyquist frequency is twice the highest frequency component in a sampled signal. In examples where the response signal is about sinusoidal, then, oversampling the response signal 130 may include sampling at greater than twice the frequency of the response signal 130. In some examples, the ADC 120 is configured to sample the response signal at about four times its frequency. The ADC 120 may be of any suitable resolution. In some examples, however, the ADC 120 may have a resolution greater than that of the DAC 110. In one example where the DAC has a 12-bit resolution, the ADC 120 may have a 16-bit resolution. Cycling the receiver circuit 104, as described herein, may allow the use of oversampling and/or of a high resolution ADC 120, which can lead to higher result quality.

The measurement system 100 may also include a DFT circuit 122. The DFT circuit 122 may be a dedicated DFT circuit and/or may be implemented in whole or in part by a Digital Signal Processor (DSP) or other suitable hardware. The DFT circuit 122 may generate a DFT of one or more sets of samples. For example, the DFT circuit 122 may generate a DFT of a set of samples captured by the ADC 120 during a sampling cycle of the receiver circuit 104. As described herein, the real component of the DFT may correspond to the ohmic resistance of the skin 126 while the imaginary component of the DFT may correspond to the reactance of the skin 126.

In some examples, the DFT circuit 122 performs an N-point Hann Sampled DFT. For example, the DFT circuit 122 may take the output of the ADC 120 as its input. The DFT circuit 122 may generate an output that includes the real and imaginary parts of the complex result in rectangular polar form. The DFT may find the real and imaginary components, for example, as indicated in Equations [1] and [2] below, where Equation [1] indicates the real component of the DFT and Equation [2] shows the imaginary component of the DFT.

$$R = \sum_{n}^{n+15} x(i) \cos\left(2 \times \pi \times i \times \frac{fout}{fADC}\right) \quad [1]$$

$$I = \sum_{n}^{n+15} x(i) \sin\left(2 \times \pi \times i \times \frac{fout}{fADC}\right) \quad [2]$$

In Equations [1] and [2], $f_{ADC}$ is the sampling frequency of the ADC; $f_{out}$ is the excitation frequency. The variable n indicates the sample in the time domain and the variable i indicates samples in the frequency domain. In the example Equations [1] and [2], the range of n is from n to n+15, indicating 16 total samples in a sample cycle. In various examples, the number of samples in a sample cycle may be modified to a number different than 16. Any suitable number of samples may be used including, for example, 16, 32, 64, 2048, etc. In some examples, the DFT circuit 122 includes or is otherwise in communication with output registers. A first output register may store the real component of the DFT, given by Equation [1] and corresponding to the ohmic resistance of the skin. A second output register may store the imaginary component of the DFT, given by Equation [2] and corresponding to the reactance of the skin. In some examples, the DFT circuit 122 or other component of the measurement system 100 may convert the output of the DFT circuit 122 to polar format, including magnitude and phase as indicated by Equations [3] and [4] below:

$$\text{Magnitude} = \sqrt{R^2 + I^2} \quad [3]$$

$$\text{Phase} = \tan^{-1}\left(\frac{I}{R}\right) \quad [4]$$

The measurement system 100 also includes a sequencer circuit 106. The sequencer circuit 106 is configured to activate and/or deactivate the excitation circuit 102, the receiver circuit 104 and/or components thereof. The sequencer circuit 106 may be or include any suitable component. In some examples, the sequencer circuit 106 includes a processor executing a software routine for activating and deactivating the receiver circuit 104 and excitation circuit 102 as described herein. Also, the sequencer circuit 106 may be or include a programmable logic array, state machine, combination of logic gates, or any other suitable hardware.

Plot 132 shows an example sequence of the excitation circuit 102 and receiver circuit 104 in the plot 132, the horizontal axis 134 corresponds to time and the vertical axis 136 corresponds to current drawn, which may be proportional to power. At an initial activation time 137, the sequencer circuit activates the excitation circuit to begin providing the excitation signal 128. Block 138 indicates the current drawn by the excitation circuit 102. An excitation setup period 142 is shown after the initial activation time. The excitation setup period 142 may be selected to allow transients from the initial activation to dissipate and to allow capacitive and/or inductive properties to skin 126, electrodes 124A, 124B, etc., to charge before measurements begin. The plot 132 also shows a sampling cycle 144. During the sampling cycle 144, the receiver circuit 104 (e.g., the ADC 120) samples the response signal 130. Any suitable number of samples may be taken during a sampling cycle.

Figure 2:
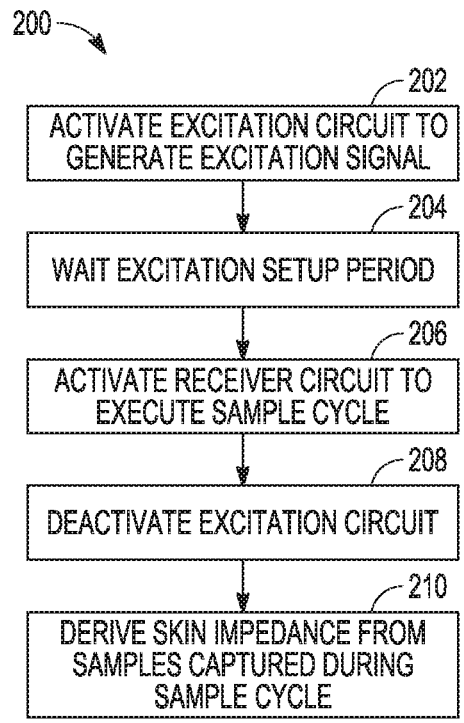
FIG. 2 is a flowchart showing one example of a process flow that may be executed by the measurement system of FIG. 1 to measure skin impedance.

FIG. 2 is a flowchart showing one example of a process flow 200 that may be executed by the measurement system 100 to measure skin impedance. The process flow 200 is described as being executed by the sequencer circuit 106. In various examples, however, the process flow 200 may be executed by any suitable component of the measurement system 100, At operation 202, the sequencer circuit 106 activates the excitation circuit 102 to generate the excitation signal 128, which is provided to the skin 126. After activating the excitation circuit 102, the sequencer circuit may wait the excitation setup time 142 at operation 204. After waiting for the excitation setup time, the sequencer circuit 106 activates the receiver circuit 104 to execute a sample cycle 144 at operation 206.

The sequencer circuit 106, at operation 208, deactivates the excitation circuit 102. In some examples, the process flow 200 is executed each time that the measurement system 100 is to measure skin impedance. At operation 210, the sequencer circuit 106 may prompt the DFT circuit 122 to find the impedance of the skin 126, for example, by finding a DFT from the set of samples of the response signal 130 collected during the sample cycle 144. In some examples, the DFT circuit 122 operates in response to an instruction signal received from the sequencer circuit 106. In other examples, the DFT circuit 122 may be configured to operate when samples collected during the sample cycle are written to a sample buffer or other memory location accessible by the DFT circuit 122. For example, when a threshold number of samples are available, the DFT circuit 122 may generate a DFT based on the available samples. In some examples, the DFT circuit 122 generates a DFT of the set of samples after the receiver circuit 104 is deactivated.

Figure 3:
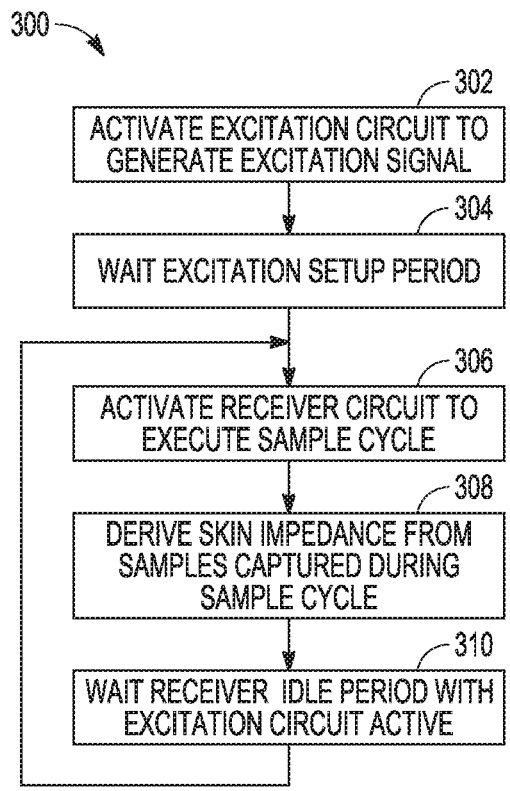
FIG. 3 is a flowchart showing another example of a process flow that may be executed by the measurement system of FIG. 1 to measure skin impedance.

FIG. 3 is a flowchart showing another example of a process flow 300 that may be executed by the measurement system 100 to measure skin impedance. Similar to the process flow 200, the process flow 300 is described as being executed by the sequencer circuit 106. In various examples, however, the process flow 200 may be executed by any suitable component of the measurement system 100. At operation 302, the sequencer circuit 106 activates the excitation circuit to generate the excitation signal 128, which is provided to the skin 126. After activating the excitation circuit 102, the sequencer circuit waits for the excitation setup time 142 to elapse at operation 304. After the excitation setup time has elapsed, the sequencer circuit activates the receiver circuit 104 to execute a sample cycle 144 at operation 306.

At operation 308, the DFT circuit 122 derives skin impedance, for example, by performing a DFT on the samples of the response signal 130 collected during the sample cycle. In the example process flow 300 of FIG. 3, however, instead of deactivating the excitation circuit 102, the sequencer circuit 106 may wait for a receiver deactivation time while keeping the excitation circuit 102 active and providing the excitation signal 128. The receiver deactivation time may be of any suitable length. When the receiver deactivation time has elapsed, the sequencer circuit 106 may once again activate the receiver circuit 104 to execute a subsequent sample cycle at operation 306, derive a skin impedance (with the DFT circuit 122) at operation 308, and wait for another receiver deactivation time at operation 310. The process flow 300 may continue in this manner as long as desired.

In one example where the output data rate (ODR) is between about 4 and 5 Hz and the excitation signal 128 and response signal 130 have a frequency of 100 Hz, the receiver sample cycle may have a duration of about 50 ms and the receiver deactivation time may be about 200 ms. This may allow four or five periods of the excitation signal per receiver sample cycle with a duty cycle of about 50 ms. At sixteen samples per sample cycle, this may result in three or four samples per period, depending on whether there are four or five periods of the excitation signal present per sampling cycle period. Setting the deactivation time to about 200 ms may keep the supply current (IDD) at less than about 100 uA. In some examples, the measurement system is configurable. As the number of samples per receiver sample cycle is increased, performance and accuracy may increase while power consumption may also increase. For example, if the number of samples per receiver sampling period is set to thirty-two (32), the receiver circuit 104 would be power up 32 times during the receiver sample cycle, which would add to the average IDD. Also, in some examples, the measurement circuit 100 may be configured with an ODR higher or lower than 4 Hz. For example, if the ODR is increased to 8 Hz, then the length of the receiver sample cycle may need to be increased to achieve the same number of samples per measurement.

Figure 4:
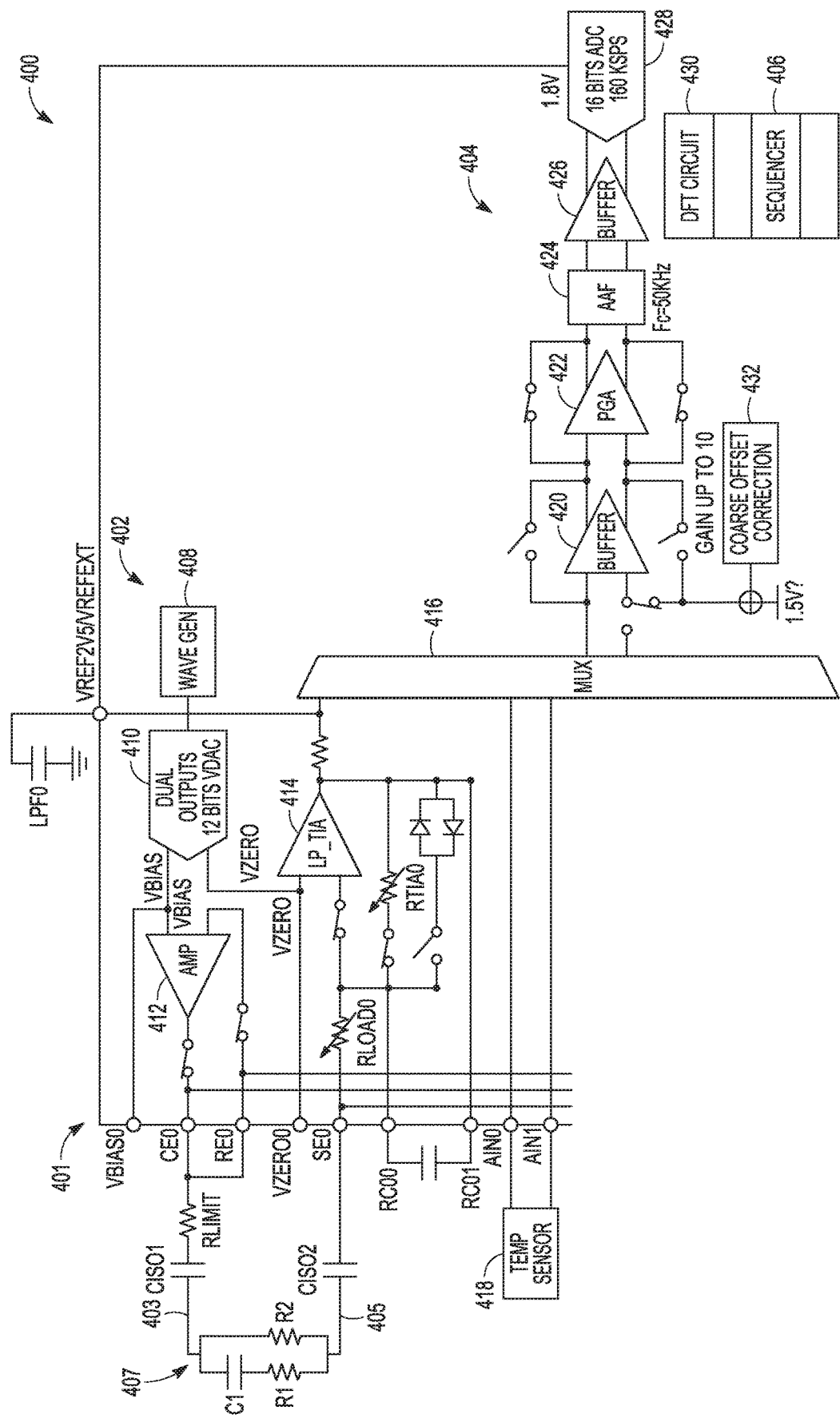
FIG. 4 is a block diagram showing one example of a measurement system for measuring skin impedance implemented on an integrated circuit.

FIG. 4 is a block diagram showing one example of a measurement system 400 for measuring skin impedance implemented on an integrated circuit 401. Any suitable integrated circuit may be used including, for example, the ADuCM350 chip, the ADuCM355 chip, or the AD5940 chip, all available from Analog Devices Inc. of Norwood, Mass. The integrated circuit 401 includes an excitation circuit 402, a receiver circuit 404, a DFT circuit 430, and a sequencer circuit 406.

The excitation circuit 402 includes a digital waveform generator 408 that generates a digital version of the excitation signal and provides the digital version of the excitation signal to the DAC 410. In the example shown, the DAC 410 has a resolution of 12-bits. The DAC 410 also provides dual outputs, a voltage $V_{bias}$ indicating the excitation signal and a reference signal called $V_{zero}$. An amplifier 412 may receive the excitation signal and provides it to skin.

From the amplifier 412, the excitation signal is provided to skin via electrode lines 403, 405. In some examples, electrode lines 403, 405 are implemented outside of the integrated circuit 401. For example, the electrode lines 403, 405 may be electrically coupled to different pints of the integrated circuit 401. An electrode lines 403, 405 may include insolation capacitor $C_{ISO1}$, $C_{ISO2}$ and a limiting resistor $R_{LIMIT}$. Isolation capacitors and limit resistors may be included to prevent the possibility of providing excessive current and/or voltage to the skin in a way that could injure the patient. In some examples, the values of the isolation capacitors and/or limit resistors are selected to meet applicable regulations. In FIG. 4, the electrodes are represented by an electrode model 407 that models the behavior of electrodes (e.g., dry electrodes) that are electrically coupled to skin. For example, the electrode model 407 includes a capacitance $C_1$ and a resistance $R_1$ in parallel with a second resistance $R_2$.

A response signal is received and provided to a transimpedance amplifier 414, which may be a component of the receiver circuit 404. For example, the transimpedance amplifier may be activated and/or deactivated with the receiver circuit 404. In some examples, described herein, the transimpedance amplifier may be activated and deactivated with the excitation circuit 402. In some examples, the transimpedance amplifier 414 is programmable to set a voltage level corresponding to the level of current of the response signal. For example, in FIG. 4 the voltage output of the transimpedance amplifier 414 for a particular level of current in the skin may be modified by modifying the value of the potentiometer $R_{load0}$. In the example of FIG. 4, the transimpedance amplifier 414 receives the $V_{zero}$ signal generated by the DAC 410 of the excitation circuit.

In the example of FIG. 4, the output of the transimpedance amplifier 414 is provided to an analog multiplex (mux) 416. The mux 416 may enable the integrated circuit 401 to utilize the receiver circuit 404 to process more than just the response signal generated in response to the excitation signal. For example, FIG. 4 also shows an example temperature sensor 418 that may generate a voltage output proportional to a temperature (e.g., a temperature of the skin, an ambient temperature, or other temperature). The output of the temperature sensor 418 may also be provided to the mux 416. Accordingly, the mux 416 may alternately provide to the receiver circuit 404 the response signal from the transimpedance amplifier 414 and/or the output of the temperature sensor.

The receiver circuit 404 includes a buffer amplifier 420 and a programmable gain amplifier 422 along with anti-aliasing filter 424 and a second buffer 426 ahead of the ADC 428. The ADC 428 may be a 16-bit ADC with a maximum sampling frequency of 160 KSPS. In some examples, the sampling frequency of the ADC 428 may be programmable, for example, by the sequencer circuit 406, as described herein. In some example, a course offset correction circuit 432 is provided, for example, to counteract drift in the DC offset of the response signal that may occur, for example, in response to changing skin conditions. Also, as shown, the buffer 420 and/or programmable gain amplifier 422 may be switchable into and/or out of the circuit.

FIG. 4 also shows a DFT circuit 430, which may calculate the DFT of samples captured during a sampling cycle of the receiver circuit 404. A sequencer circuit 406 may manage the sequencing of the excitation circuit 402 and/or receiver circuit 404, for example, as described herein with respect to FIGS. 2 and 3. The sequencer circuit 406, in some examples, is programmable to set, for example, the excitation setup time, the deactivation time, the number of samples taken during a sample cycle, etc. In some examples, the sequencer circuit 406 and DFT circuit 430 may be part of a core of the integrated circuit 401. For example, the DFT circuit 430 may be part of the integrated circuit 401 and may not be implemented at a separate Digital Signal Processor (DSP) or other processor.

Figure 5:
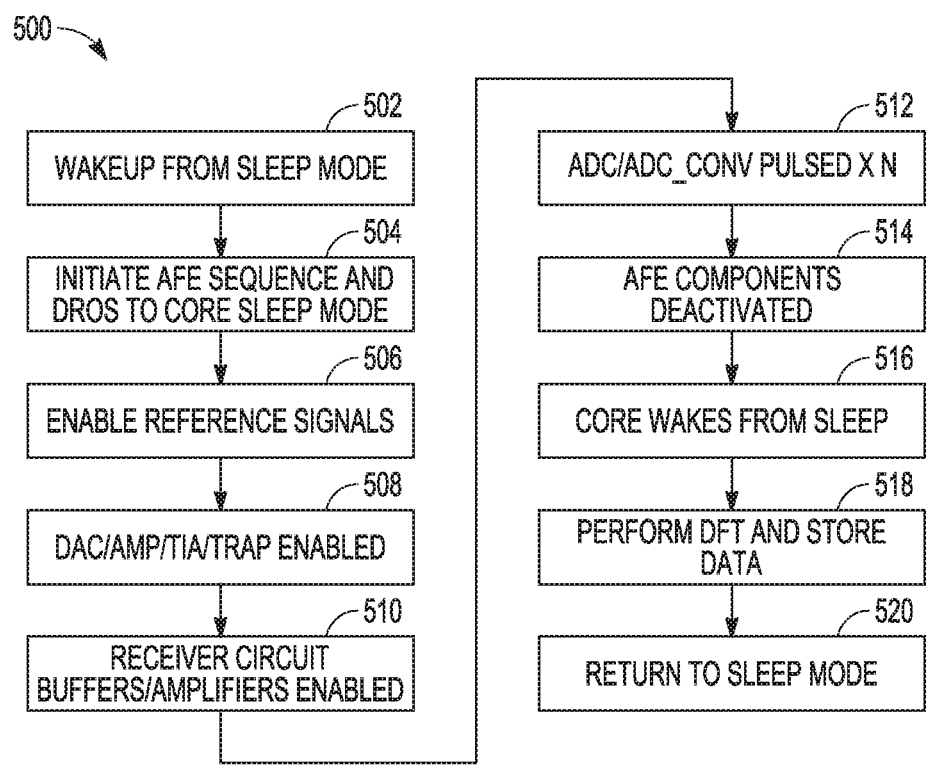
FIG. 5 is a flowchart showing one example of a process flow that may be executed by a measurement system to measure skin impedance.
Figure 6:
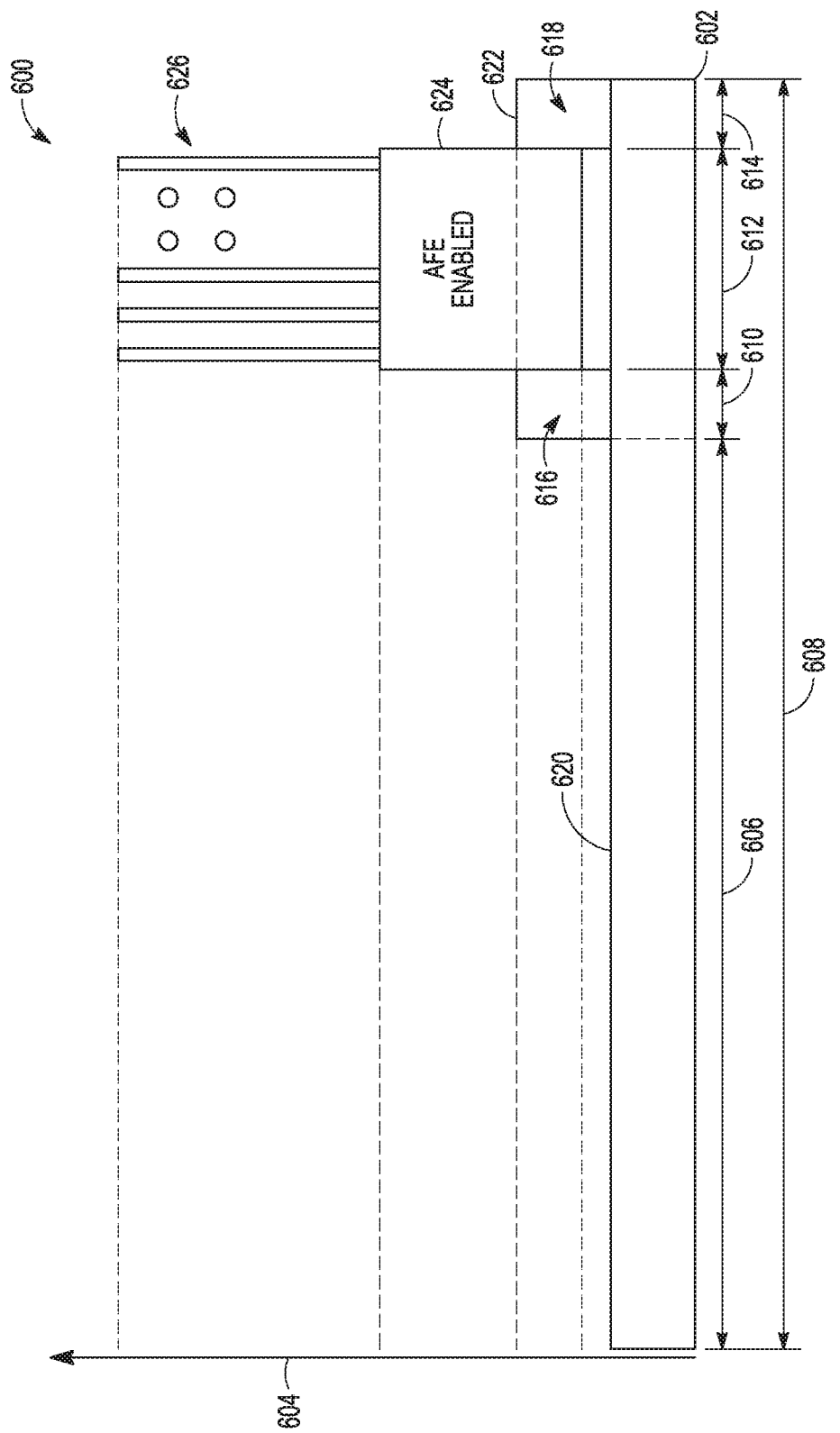
FIG. 6 is a plot showing one example of the current drawn by a measurement system executing the process flow of FIG. 5.

FIG. 5 is a flowchart showing one example of a process flow 500 that may be executed by a measurement system to measure skin impedance. The process flow 500 may be executed by a measurement system such as the measurement system 100 of FIG. 1 or the measurement system 400 of FIG. 4. FIG. 6 is a plot 600 showing one example of the current drawn by a measurement system executing the process flow 500. The plot 600 is similar to the plot 132 of FIG. 1 but shows additional details of an example implementation. The plot 600 includes a horizontal axis 602 indicating time and a vertical axis 604 indicating current drawn by the measurement system. The current drawn by the measurement system may be proportional to the power consumed by the measurement system.

In the example of FIGS. 5 and 6, the measurement system executes a sleep mode. In the sleep mode, unused components of the measurement system, such as the excitation circuit, the receiver circuit, etc., are deactivated to save power. Components that draw current while the measurement system is in the sleep mode may include, for example, an oscillator, a clock generator, memory, etc. Referring to FIG. 6, current 620 is drawn while the measurement system is in sleep mode. Current 620 may persist while the measurement system is active. The measurement system may remain in the sleep mode for a time 606. In one example in which the excitation signal has a frequency of about 100 Hz, the time 606 may be about 200 ms. The total time 608 may be about 250 ms.

Referring now to FIG. 5, when the time 606 has passed, the measurement system wakes up from the sleep mode at operation 502. When the measurement system wakes up from the sleep mode, core components of the measurement system may begin drawing current. For example, referring to FIG. 6, current 616 may be drawn by core components that are activated after the measurement system wakes up from the sleep mode. Core components may include the sequencer circuit, the DFT circuit, etc. In some examples, core components are positioned at a core of an integrated circuit implementing the measurement system.

Upon wakeup at operation 502, the sequencer circuit may initiate an analog front end (AFE) sequence and drop some or all the core components into a core sleep mode. The AFE may include, for example, the excitation circuit and the receiver circuit. During the core sleep mode, some or all of the core components may be deactivated. For example, the DFT circuit may be deactivated during a sampling cycle. Referring to FIG. 6, the current drawn by the core components is higher at 616 for a time 610 when the AFE sequence is initiated and then drops for a time 612 while the AFT is enabled. For example, the sequencer circuit may awaken and draw current to initiate the wakeup of the AFE. While the AFE is executing a sampling cycle, the sequencer circuit may draw less current (time 612). After the AFE sequence, the DFT circuit may be activated to determine a DFT of the samples captured during the sample cycle.

The current 624 in FIG. 6 is drawn by the excitation circuit and receiver circuit during the AFE sequence. The AFE sequence may include powering up the excitation circuit and the receiver circuit to generate the excitation signal and capture the response signal. In some examples, the AFE sequence may include activating components of the excitation and receiver circuits in an order that permits the respective circuits to generate the excitation signal and measure the response signal. For example, at operation 506, reference signals may be enabled. Reference signals may include, for example, reference voltages, bias voltages, regulators, such as drop out regulators, etc. At operation 508, the DAC of the excitation circuit may be enabled along with the transimpedance amplifier of the receiver circuit. At operation 510, buffers and remaining amplifiers of the receiver circuit are activated.

Next, at operation 512, the ADC of the receiver circuit executes a sample cycle by pulsing N times to capture N samples of the response signal. Current drawn by the ADC while collecting samples is indicated by current pulses 626 in FIG. 6. N may be any suitable number such as, for example, sixteen (16). In some examples, the number of samples generated during a sample cycle can be configured by a designer. This may allow the designer to trade-off between power consumption and more accurate measurements of skin impedance. In the example, described above with a 100 Hz excitation signal, a sample size of 2048 samples may provide an accuracy of about 100 dB at 6 mA. Reducing the sampling cycle set size to 16 samples, however, may only reduce the accuracy of the measurement to 77 dB. As described herein, the ADC may be configured to oversample the response signal during the sample cycle.

In some examples, a skin impedance measurement is susceptible to noise around 50 or 60 Hz. The measurement system, in some examples, includes a filter for reducing this 50/60 Hz noise. In other examples, the frequency of the excitation signal, the number of samples taken in a sample cycle, and the sampling frequency may be selected in a manner that causes the DFT operation performed by the DFT circuit to filter 50/60 Hz noise. For example, when the frequency of the excitation signal may be set at a frequency other than 50 Hz or 60 Hz, the DFT operation may reject noise at 50 Hz and/or 60 Hz.

When the sample cycle is complete, the AFE components (e.g., the excitation circuit and receiver circuit) may be deactivated at operation 514. For example, to deactivate the AFE, the operations 506, 508, and 510 may be reversed. The core components may wakeup from the core sleep mode at operation 516. Referring again to FIG. 6, this is indicated by the increase in the current 622 drawn by the core components at 618. At operation 518, the DFT circuit may generate a DFT from the set of samples collected during the sample cycle, where the real and imaginary components of the DFT correspond to the ohmic resistance and reactance of the skin. The DFT circuit or other suitable circuit may write results to a memory location that can be accessed, for example, by a processor. At operation 520, the measurement system may return to the sleep mode and may draw only current 620.

Figure 7:
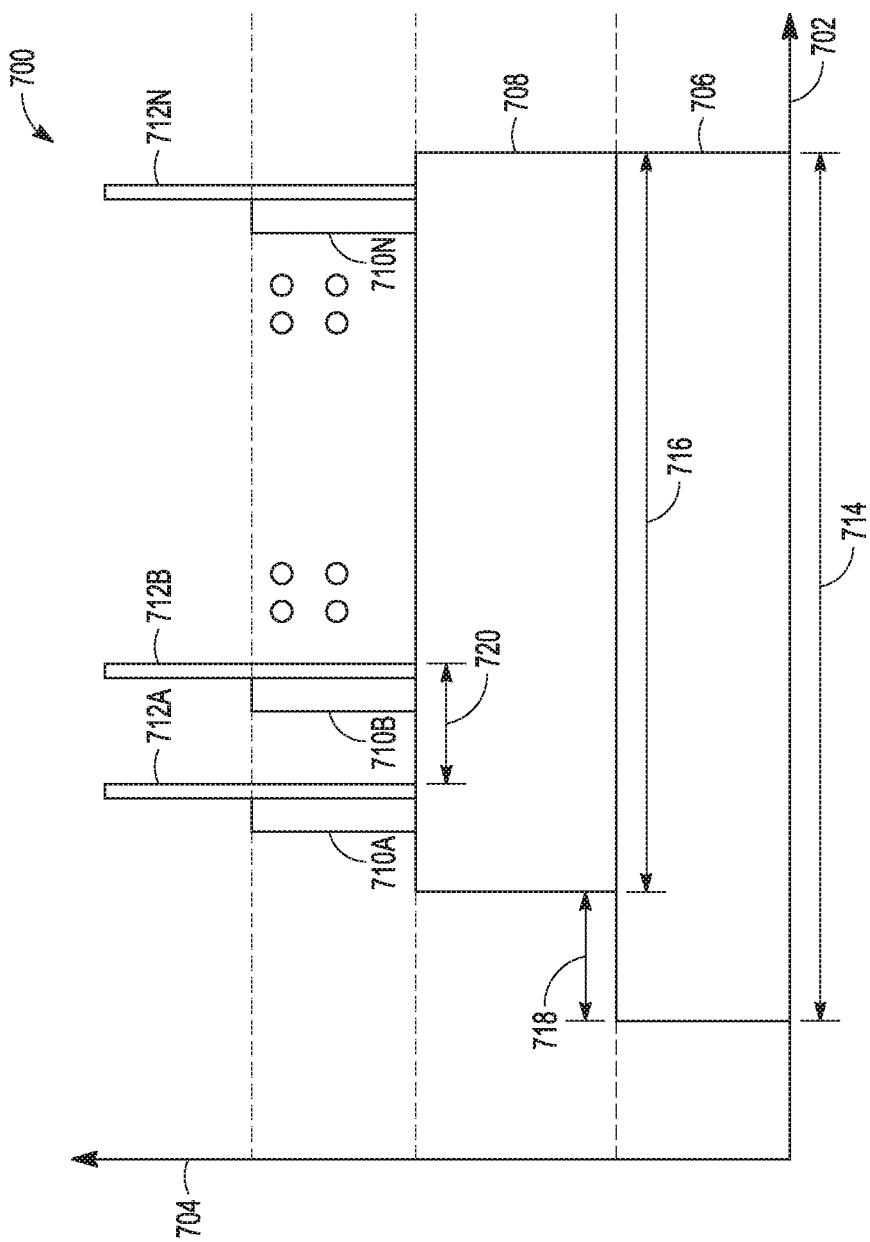
FIG. 7 is plot showing another example of current drawn by a measurement system during a sample cycle.

FIG. 7 is plot 700 showing another example of current drawn by a measurement system during a sample cycle. Like the plot 600, the plot 700 includes a horizontal axis 702 indicating time and a vertical axis 704 indicating current. The plot 700 may describe the behavior of any suitable measurement system such as, for example, the measurement system 100 of FIG. 1 or the measurement system 400 of FIG. 4.

In the plot 700, current 706 is drawn by circuits generating reference signals. After a reference signal start-up time 718, the excitation circuit may begin drawing current 708. In some examples, portions of the receiver circuit, such as the transimpedance amplifier, may be activated at the same time as the excitation circuit. When an excitation setup period has passed, the receiver circuit may execute a sample cycle. The sample cycle is indicated by currents 710A, 712A, 710B, 712B, 710N, 712N. For example, currents 710A, 710B, 710N may represent current drawn by the receiver circuit when the ADC is not actively sampling. The time between samples (e.g., currents 710A-N and currents 712A-N) may depend on the leCurrents 712A, 712B, 712N may indicate current drawn by the ADC when the ADC is actively sampling the response signal. The total time that the excitation signal is activated may be indicated by time 716. The total time that the excitation circuit and receiver circuit are activated may be indicated by time 714. In an example where the frequency of the excitation signal is about 100 Hz, the total time 714 may be about 52 ms and the time 716 may be about 50 ms.

Figure 8:
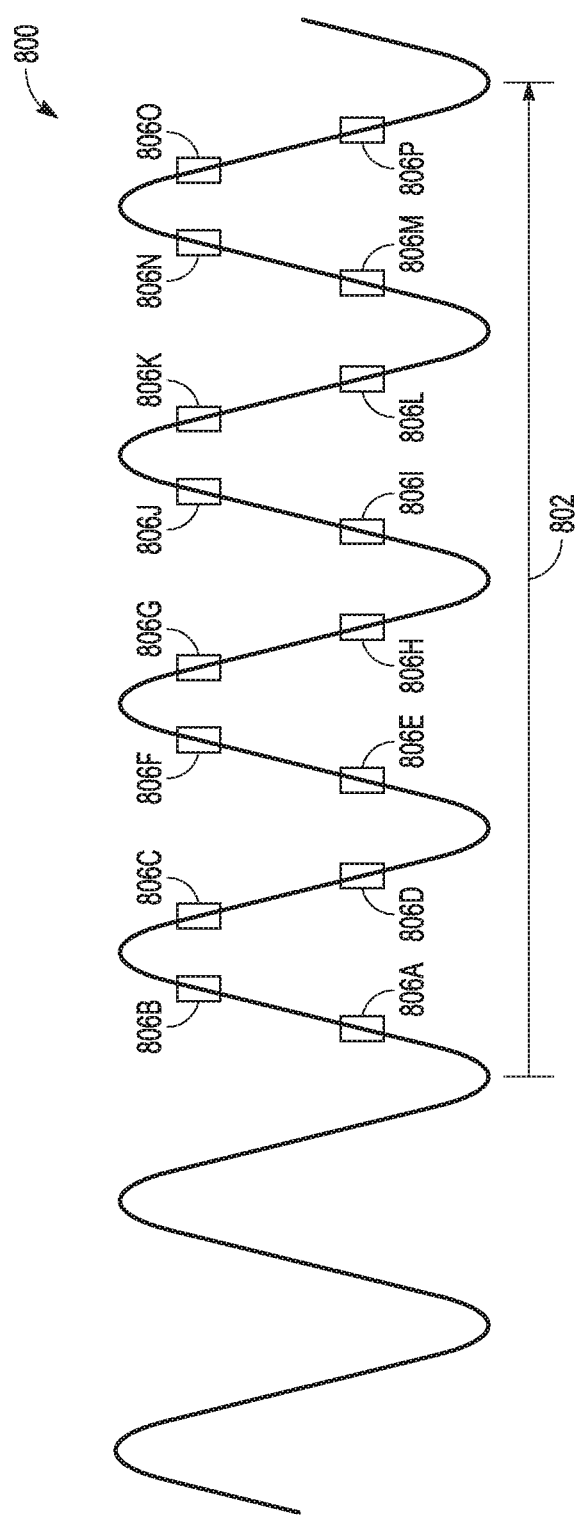
FIG. 8 shows an example response signal illustrating a sampling cycle synchronized to the response signal frequency.

In some examples, sample cycles executed by the receiver circuit are synchronized with the excitation signal and the response signal. In this way, a sample set for generating a DFT may sample common portions of the period of the respective signals. FIG. 8 shows an example response signal 800 illustrating a sampling cycle 802 synchronized to the response signal frequency. An example sample cycle 802 includes four periods of the response signal 800. FIG. 8 illustrates samples 806A-P, which indicate portions of the response signal that are sampled during an example sample cycle. In the example of FIG. 8, sixteen samples are taken over the four periods of the response signal that are part of the sample. In some examples, the sampling frequency may be an integer multiple of the response signal frequency. This may cause samples taken within a sample cycle to include samples taken at common positions of the response signal period and, if maintained over multiple sample cycles, may cause samples taken across sample cycles to include samples taken at common positions of the response signal. In the example of FIG. 8, sixteen samples over four periods of the response signal, indicating that the sampling frequency may be about 4 times the frequency of the response signal. (E.g., the response signal may have the same frequency as the excitation signal, albeit with a different magnitude and a phase difference.)

Figure 9:
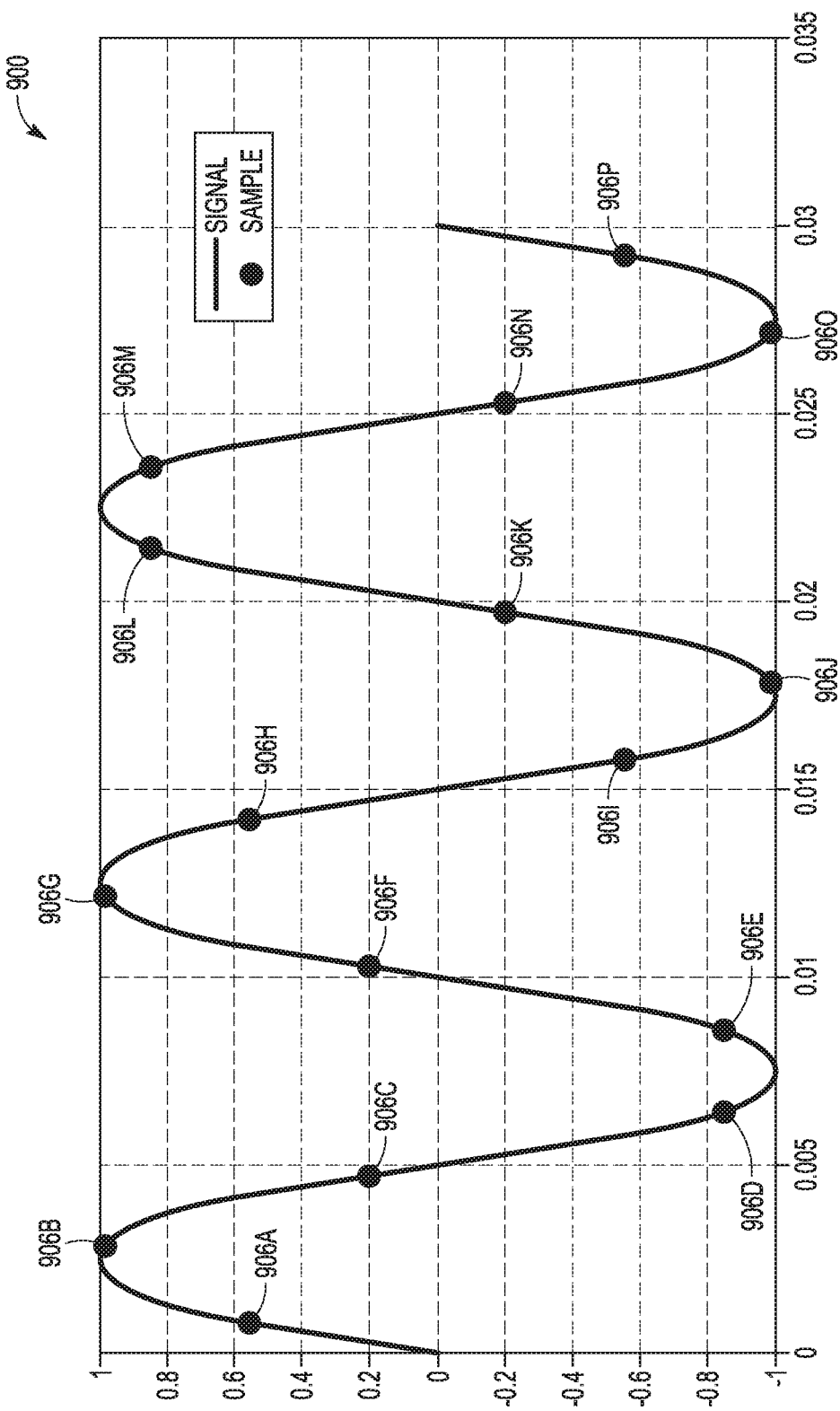
FIG. 9 shows an example response signal illustrating a sampling cycle that is asynchronous relative to the response signal frequency.

In some examples, sample cycles executed by the receiver circuit are asynchronous with respect to the excitation signal and the response signal. FIG. 9 shows an example response signal 900 illustrating a sampling cycle 902 that is asynchronous relative to the response signal frequency. An example sample cycle 902 includes three periods of the response signal 900. FIG. 9 illustrates samples 906A-P, which indicate portions of the response signal that are sampled during an example sample cycle. In the example of FIG. 9, sixteen samples are taken over the three periods of the response signal that are part of the sample. Although three periods of the response signal 900 are shown in FIG. 9, in some examples, the sample cycle may include more or fewer than three periods including, for example, two periods, five periods, etc.

Figure 10:
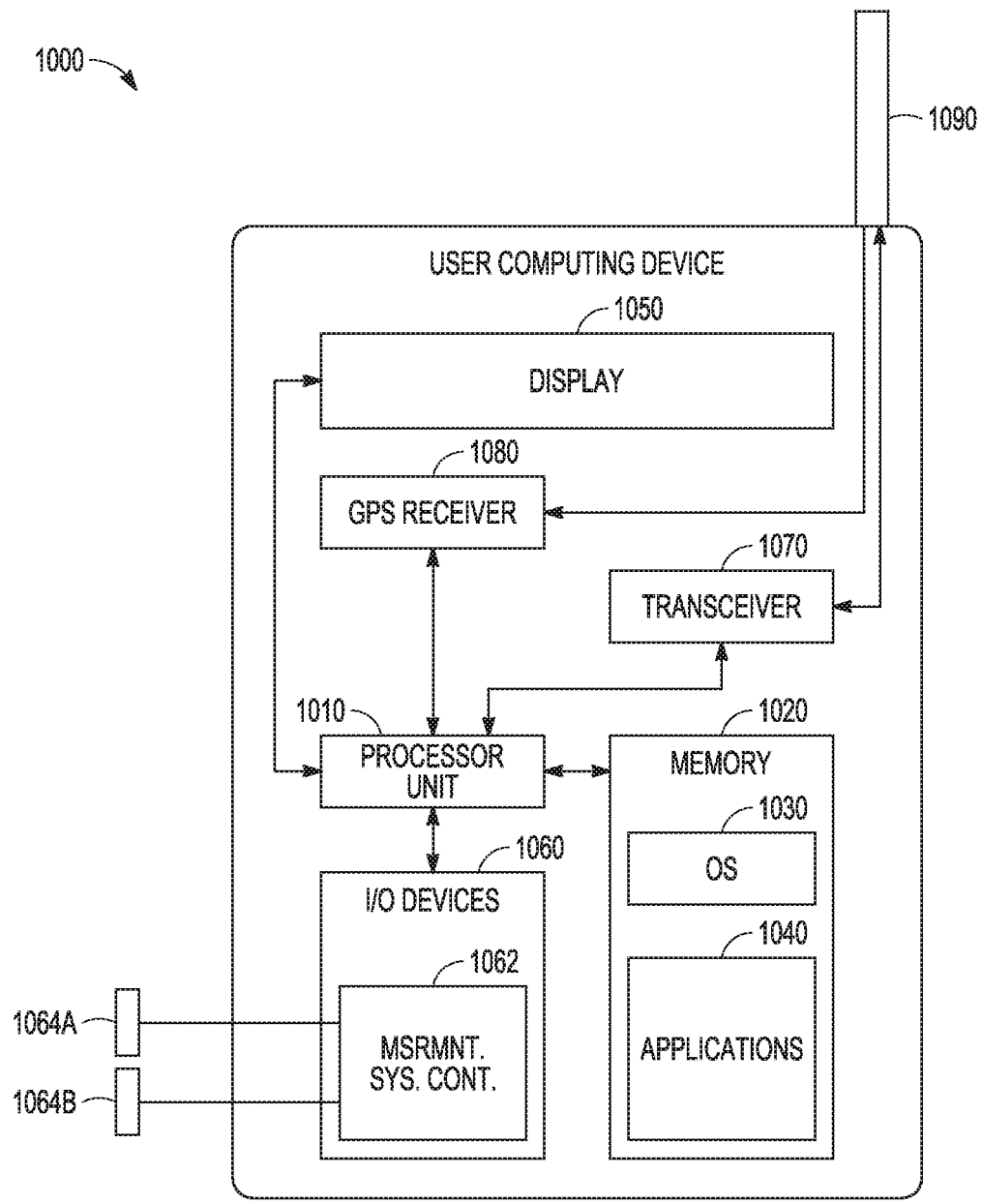
FIG. 10 is a block diagram showing an example architecture of a computing device including a measurement system as described herein.

FIG. 10 is a block diagram showing an example architecture of a computing device 1000 including a measurement system as described herein. The computing device may be or include any suitable device that measures skin impedance, for example, as an indicator of EDA. In one example, the computing device is a wearable device mounted on a band like a wrist watch, a clip that clips to clothing, an adhesive that sticks to the skin or other suitable mechanism for brining electrodes 1064A, 1064B into contact with the skin, etc.

The computing device comprises a processor unit 1010. The processor unit 1010 may include one or more processors. Any of a variety of different types of commercially available processors suitable for user computing devices may be used (for example, an XScale architecture microprocessor, a Microprocessor without Interlocked Pipeline Stages (MIPS) architecture processor, or another type of processor). A memory 1020, such as a Random Access Memory (RAM), a Flash memory, or other type of memory or data storage, is typically accessible to the processor. The memory 1020 may be adapted to store an operating system (OS) 1030, as well as application programs 1040.

The processor unit 1010 may be coupled, either directly or via appropriate intermediary hardware, to a display 1050 and to one or more input/output (I/O) devices 1060, such as a keypad, a touch panel sensor, a microphone, and the like. Such I/O devices 1060 may include a touch sensor for capturing fingerprint data, a camera for capturing one or more images of the user, a retinal scanner, or any other suitable devices.

In some examples, the I/O devices include a measurement system controller 1062 in communication with electrodes 1064A, 1064B to implement a measurement system as described herein. In some examples, the measurement system controller 1062 comprises an integrated circuit, such as the integrated circuit 401 of FIG. 4. The integrated circuit 401 may be mounted on a controller board and/or motherboard of the computing device. The controller board and/or motherboard may include components such as limit resistors, isolation capacitors, etc. The measurement system controller 1062 may also comprise a DFT circuit, similar to those described herein, that generates a DFT from samples captured during a sample cycle, as described herein. For example, the DFT circuit may write the real and imaginary portions of the DFT, corresponding to ohmic resistance and reactance of the skin, to a set of registers. The processor unit 1010 may read the real and imaginary portions of the DFT from the registers.

In some examples, the processor unit 1010 may be coupled to a transceiver 1070 that interfaces with an antenna 1090. The transceiver 1070 may be configured to both transmit and receive cellular network signals, wireless data signals, or other types of signals via the antenna 1090, depending on the nature of the user computing device implemented by the computing device. Although one transceiver 1070 is shown, in some examples, the computing device includes additional transceivers. For example, a wireless transceiver may be utilized to communicate according to an IEEE 802.11 specification, such as Wi-Fi and/or a short-range communication medium such as Bluetooth®, etc. Some short-range communication mediums, such as NEC, may utilize a separate, dedicated transceiver. Further, in some configurations, a Global Positioning System (GPS) receiver 1080 may also make use of the antenna 1090 to receive GPS signals. In addition to or instead of the GPS receiver 1080, any suitable location-determining sensor may be included and/or used including, for example, a Wi-Fi positioning system. In some examples, the architecture (e.g., processor unit 1010) may also support a hardware interrupt. In response to a hardware interrupt, the processor unit 1010 may pause its processing and execute an interrupt service routine (ISR).

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or " " are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The term "circuit" can include a dedicated hardware circuit, a general-purpose microprocessor, digital signal processor, or other processor circuit, and may be structurally configured from a general purpose circuit to a specialized circuit such as using firmware or software.

Any one or more of the techniques methodologies) discussed herein may be performed on a machine. In various embodiments, the machine may operate as a standalone device or may be connected (e.g., networked) to other machines. In a networked deployment, the machine may operate in the capacity of a server machine, a client machine, or both in server-client network environments. In an example, the machine may act as a peer machine in peer-to-peer (P2P) (or other distributed) network environment. The machine may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions can enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Particular implementations of the systems and methods described herein may involve use of a machine (e.g., computer system) that may include a hardware processor (e.g., a central processing unit (CPU), a graphics processing unit (GPU), a hardware processor core, or any combination thereof), a main memory and a static memory, some or all of which may communicate with each other via an interlink (e.g., bus). The machine may further include a display unit, an alphanumeric input device (e.g., a keyboard), and a user interface (UI) navigation device (e.g., a mouse). In an example, the display unit, input device and UI navigation device may, be a touch screen display. The machine may additionally include a storage device (e.g., drive unit), a signal generation device (e.g., a speaker), a network interface device, and one or more sensors, such as a global positioning system (GPS) sensor, compass, accelerometer, or other sensor. The machine may include an output controller, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device may include a machine readable medium on which is stored one or more sets of data structures or instructions (e.g., software) embodying or utilized by any one or more of the techniques or functions described herein. The instructions may also reside, completely or at least partially, within the main memory, within static memory, or within the hardware processor during execution thereof by the machine. In an example, one or any combination of the hardware processor, the main memory, the static memory, or the storage device may constitute machine readable media.

While the machine readable medium can include a single medium, the term "machine readable medium" may include a single medium or multiple media (e.g., a centralized or distributed database, and/or associated caches and servers) configured to store the one or more instructions.

The term "machine readable medium" may include any medium that is capable of storing, encoding, or carrying instructions for execution by the machine and that cause the machine to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions may further be transmitted or received over a communications network using a transmission medium via the network interface device utilizing any one of a number of transfer protocols (e.g., frame relay, internee protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IFEE 802.15.4 family of standards, peer-to-peer (P2P) networks, among others. In an example, the network interface device may include one or more physical jacks (e.g., Ethernet, coaxial, or phone jacks) or one or more antennas to connect to the communications network. In an example, the network interface device may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine, and includes digital or analog communications signals or other intangible medium to facilitate communication of such software.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A measurement system for measuring an electrical property of skin, comprising:
    an excitation circuit comprising a digital waveform generator to generate a periodic excitation signal that, when provided to the skin, generates a response signal in the skin indicative of the electrical property;
    a receiver circuit comprising an analog-to-digital converter (ADC); and
    a sequencer circuit configured to perform operations comprising:
        activate the excitation circuit to provide the excitation signal to the skin;
        while the excitation circuit is activated to provide the excitation signal to the skin, activating the receiver circuit to execute a first sample cycle to generate a first plurality of samples of the response signal, wherein the receiver circuit oversamples the response signal during the first sample cycle;
        after the receiver circuit executes the first sample cycle, deactivating the receiver circuit;
        after the deactivating of the receiver circuit and while the excitation circuit is activated to provide the excitation signal to the skin, reactivating the receiver circuit to execute a second sample cycle to generate a second plurality of samples of the response signal;
        determining a first value for the electrical property of the skin based at least in part on the first plurality of samples of the response signal; and
        determining a second value for the electrical property of the skin based at least in part on the second plurality of samples of the response signal.

2. The measurement system of claim 1, wherein the receiver circuit is configured to perform operations comprising:
   capturing a first sample of the first plurality of samples when the excitation signal is at a first position of a response signal period;
   capturing a second sample of the first plurality of samples when the excitation signal, is at a second position of the response signal period;
   capturing a first sample of the second plurality of samples when the excitation signal is at the first position of the response signal period; and
   capturing a second sample of the second plurality of samples when the excitation signal is at the second position of the response signal period.

3. The measurement system of claim 1, wherein the first sample cycle is executed after an excitation setup time has elapsed since the activating of the excitation circuit.

4. The measurement system of claim 1, wherein the sequencer circuit is further configured to perform operations comprising:
   deactivating the excitation circuit after the receiver circuit executes the first sample cycle; and
   reactivating the excitation circuit, wherein the reactivating the receiver circuit is after the reactivating of the excitation circuit by an excitation setup time.

5. The measurement system of claim 1, further comprising a discrete Fourier transform (DFT) circuit configured to determine a DFT of the response signal based at least in part on the first plurality of samples.

6. The measurement system of claim 5, wherein the DFT circuit is further configured to generate a real component of the DFT of the response signal corresponding to an ohmic resistance of the skin and an imaginary component of the DFT corresponding to a reactance of the skin.

7. The measurement system of claim 1, wherein a sampling frequency of the ADC is more than twice a frequency of the excitation signal.

8. The measurement system of claim 1, wherein a sampling frequency of the ADC is at least four times a frequency of the excitation signal.

9. The measurement system of claim 1, wherein the receiver circuit draws a first current level when deactivated, a second current level when activated and not actively sampling the response signal, and a third current level when activated and actively sampling the response signal, wherein the third current level is higher than the second current level, and wherein the second current level is greater than the first current level.

10. A method for measuring an electrical property of skin, comprising:
   activating an excitation circuit to provide a periodic excitation signal to the skin; wherein the excitation signal, when provided to the skin, generates a response signal in the skin indicative of the electrical property;
   while the excitation circuit is activated to provide the excitation signal to the skin, activating a receiver circuit to execute a first sample cycle to generate a first plurality of samples of the response signal;
   oversampling the response signal during the first sample cycle;
   after the receiver circuit executes the first sample cycle, deactivating the receiver circuit;
   after the deactivating of the receiver circuit and while the excitation circuit is activated to provide the excitation signal to the skin, reactivating the receiver circuit to execute a second sample cycle to generate a second plurality of samples of the response signal;
   determining a first value for the electrical property of the skin based at least in part on the first plurality of samples of the response signal; and
   determining a second value for the electrical property of the skin based at least in part on the second plurality of samples of the response signal.

11. The method of claim 10, further comprising:
   capturing a first sample of the first plurality of samples when the excitation signal is at a first position of a response signal period;
   capturing a second sample of the first plurality of samples when the excitation signal is at a second position of the response signal period;
   capturing a first sample of the second plurality of samples when the excitation signal is at the first position of the response signal period; and
   capturing a second sample of the second plurality of samples when the excitation signal is at the second position of the response signal period.

12. The method of claim 10, further comprising waiting for an excitation setup time after the activating of the excitation circuit before executing the first sample cycle.

13. The method of claim 10, further comprising:
   deactivating the excitation circuit after the receiver circuit executes the first sample cycle; and
   reactivating the excitation circuit, wherein the reactivating the receiver circuit is after the reactivating of the excitation circuit by an excitation setup time.

14. The method of claim 10, further comprising determining a DFT of the response signal based at least in part on the first plurality of samples.

15. The method of claim 14, further comprising determining a real component of the DFT of the response signal corresponding to an ohmic resistance of the skin and an imaginary component of the DFT corresponding to a reactance of the skin.

16. The method of claim 10, wherein executing the first sample cycle comprises operating an ADC at more than twice a frequency of the excitation signal.

17. The method of claim 10, wherein executing the first sample cycle comprises operating an ADC at greater than four times a frequency of the excitation signal.

18. The method of claim 10, wherein the receiver circuit draws a first current level when deactivated, a second current level when activated and not actively sampling the response signal, and a third current level when activated and actively sampling the response signal, wherein the third current level is higher than the second current level, and wherein the second current level is greater than the first current level.

19. A computing device for measuring an electrical property of skin, comprising:
   a first electrode;
   a second electrode; and
   a measurement system unit in communication with, the first electrode and the second electrode, wherein the measurement system unit comprises:
   an excitation circuit comprising a digital waveform generator to generate a periodic excitation signal that, when provided to the skin, generates a response signal in the skin indicative of the electrical property;
   a receiver circuit comprising an analog-to-digital converter (ADC); and
   a sequencer circuit configured to perform operations comprising:

activate the excitation circuit to provide the excitation signal to the skin;
- while the excitation circuit is activated to provide the excitation signal to the skin, activating the receiver circuit to execute a first sample cycle to generate a first plurality of samples of the response signal, wherein the receiver circuit oversamples the response signal during the first sample cycle;
- after the receiver circuit executes the first sample cycle, deactivating the receiver circuit;
- after the deactivating of the receiver circuit and while the excitation circuit is activated to provide the excitation signal to the skin, reactivating the receiver circuit to execute a second sample cycle to generate a second plurality of samples of the response signal;
- determining a first value for the electrical property of the skin based at least in part on the first plurality of samples of the response signal; and
- determining a second value for the electrical property of the skin based at least in part on the second plurality of samples of the response signal.

20. The computing device of claim 19, wherein the receiver circuit is configured to perform operations comprising:

- capturing a first sample of the first plurality of samples when the excitation signal is at a first position of a response signal period;
- capturing a second sample of the first plurality of samples when the excitation signal is at a second position of the response signal period;
- capturing a first sample of the second plurality of samples when the excitation signal is at the first position of the response signal period; and
- capturing a second sample of the second plurality of samples when the excitation signal is at the second position of the response signal period.

21. The computing device of claim 19, wherein the receiver circuit draws a first current level when deactivated, a second current level when activated and not actively sampling the response signal, and a third current level when activated and actively sampling the response signal, wherein the third current level is higher than the second current level, and wherein the second current level is greater than the first current level.

* * * * *

UNITED STATES PATENT AND TRADEMARK OFFICE
CERTIFICATE OF CORRECTION

PATENT NO. : 10,702,184 B2
APPLICATION NO. : 15/616807
DATED : July 7, 2020
INVENTOR(S) : Riordan et al.

Page 1 of 1

It is certified that error appears in the above-identified patent and that said Letters Patent is hereby corrected as shown below:

On the Title Page

On page 2, in Column 2, under "Other Publications", Line 17, delete "Electroderrnal" and insert --Electrodermal-- therefor In the Claims In Column 17, Line 8, in Claim 2, delete "signal," and insert --signal-- therefor In Column 17, Line 54, in Claim 10, delete "skin;" and insert --skin,-- therefor Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*